(12) United States Patent
Lee et al.

(10) Patent No.: US 6,689,913 B2
(45) Date of Patent: Feb. 10, 2004

(54) PROCESS FOR PREPARING TERBINAFINE AND HCl SALT THEREOF

(75) Inventors: Tai-Au Lee, Seoul (KR); Kyu-Jung Wang, Seoul (KR); Hong-Bae Kim, Kyonggi-do (KR); Kyoung-Chan Kwon, Kyonggi-do (KR); Chang-Hoe Ku, Seoul (KR)

(73) Assignee: Yuhan Corporation (KR)

( * ) Notice: Subject to any disclaimer, the term of this patent is extended or adjusted under 35 U.S.C. 154(b) by 0 days.

(21) Appl. No.: 10/330,927

(22) Filed: Dec. 27, 2002

(65) Prior Publication Data

US 2003/0130530 A1 Jul. 10, 2003

(30) Foreign Application Priority Data

Dec. 28, 2001 (KR) ........................................ 2001-86713

(51) Int. Cl.$^7$ ........................ C07C 209/00; C07C 211/27
(52) U.S. Cl. ..................... 564/337; 564/387; 564/397
(58) Field of Search ................................ 564/337, 387, 564/397

(56) References Cited

U.S. PATENT DOCUMENTS

| 5,440,049 A | 8/1995 | Nakagawa et al. ............ 549/49 |
| 5,817,875 A | 10/1998 | Karimian et al. ............ 564/387 |

FOREIGN PATENT DOCUMENTS

| EP | 0 024 587 | 8/1980 |

OTHER PUBLICATIONS

Stutz, et al. "Synthesis and Antifungal Activity of (E)–N–(6, 6–Dimethyl–2–hepten–4–ynyl)–N–methyl–1–naphthalenemethanamine (SF86–327) and Related allylamine Derivatives with Enhanced Oral Activity", J. Med. Chem. vol. 27. pp. 1539–1543. (1984).
KR 1020000065691. Publication Date. Nov. 15, 2000. Korean Patent Abstracts.

Primary Examiner—Brian Davis
(74) Attorney, Agent, or Firm—Cantor Colburn LLP

(57) ABSTRACT

Provided is a process for preparing terbinafine or its HCl salt comprising: reacting a furan derivative with a base to form a second compound; performing a reductive alkylation of the second compound obtained in the step with N-methyl-1-naphthalenemethylamine or its HCl salt to form a third compound; and purifying the third compound.

13 Claims, No Drawings

PROCESS FOR PREPARING TERBINAFINE AND HCl SALT THEREOF

CROSS REFERENCE TO RELATED APPLICATIONS

This application is based upon and claims priority from Korean Patent Application No. 2001-86713 filed Dec. 28, 2001, the contents of which are incorporated herein in its entirety by reference.

BACKGROUND OF THE INVENTION

1. Field of the Invention

The present invention relates to a process for preparing terbinafine and its HCl salt useful as an anti-fungal agent.

2. Description of the Related Art

Terbinafine or its HCl salt is a compound useful as an anti-fungal agent. The chemical name of terbinafine is trans-N-methyl-N-(1-naphthylmethyl)-6,6-dimethylhept-2-en-4-ynyl-1-amine, represented by the following chemical structure.

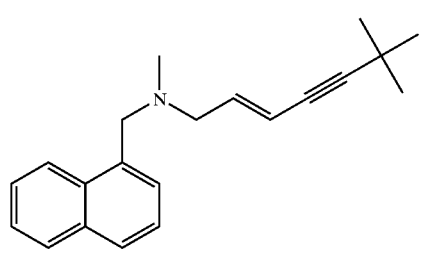

Conventional processes for preparing terbinafine or its HCl salt are disclosed in European Pat. No. 24,587, U.S. Pat. No. 5,440,049, U.S. Pat. No. 5,817,875, *J. Med. Chem.*, 27, 1539 (1984), and Korean Laid-open Pub. No. 2000-65,691.

The process disclosed in European Pat. No. 24,587 may be summarized as following reaction schemes 1 and 2:

Reaction Scheme 1

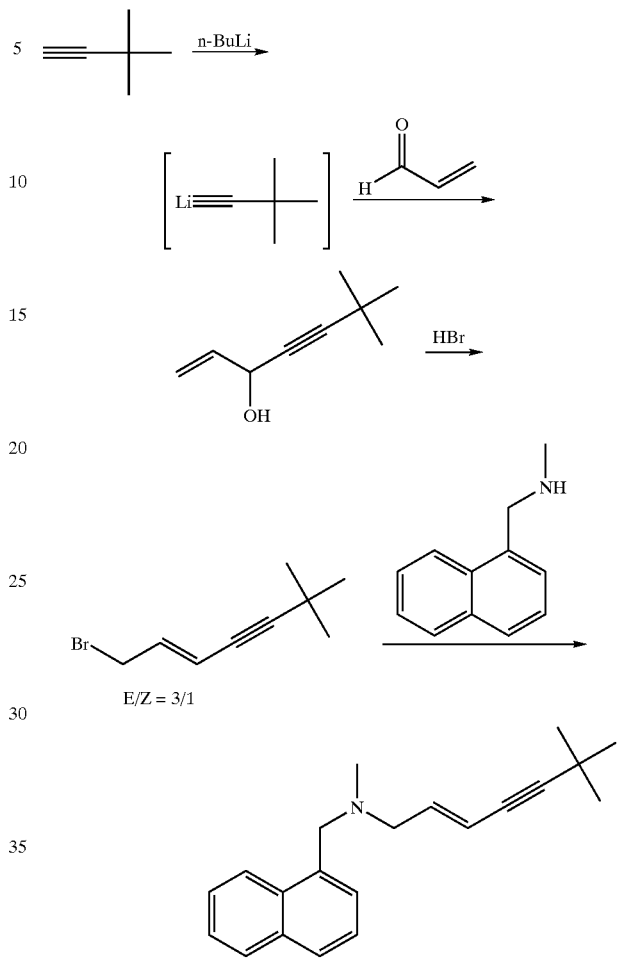

Reaction Scheme 2

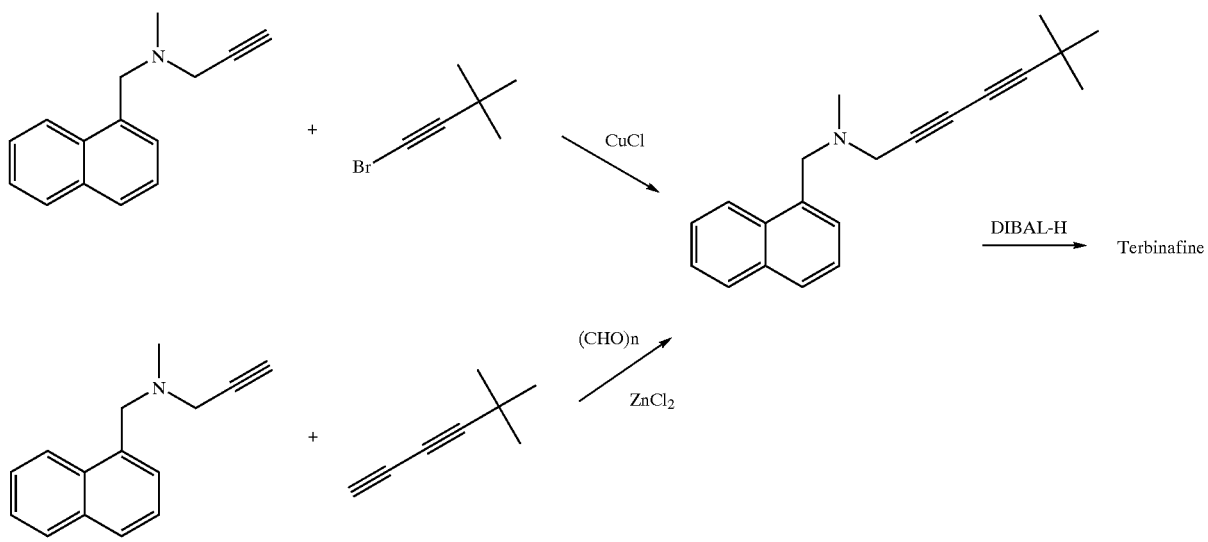

In the above process according to the reaction scheme 1, the bromoenyne derivative, intermediate for the preparation of terbinafine, is obtained unfavorably in a mixture form having an E/Z ratio of 3/1. Further, n-butyllithium, which is a strong base difficult to be available for industrial use, is used and the process is completed through so many complicated steps. Accordingly, the process in accordance with the reaction scheme 1 has difficulties to be applied to an industrial-scale mass production.

The process according to the reaction scheme 2 gives a by-product, which decreases the yield of terbinafine. Further, diisobutylaluminum hydride (DIBAL-H), which is a strong reducing agent, is used, which is unfavorable for industrial-scale mass production.

The process disclosed in U.S. Pat. No. 5,440,049 may be summarized as following reaction scheme 3:

Reaction Scheme 3

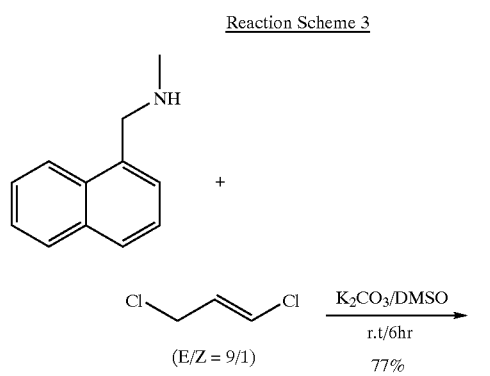

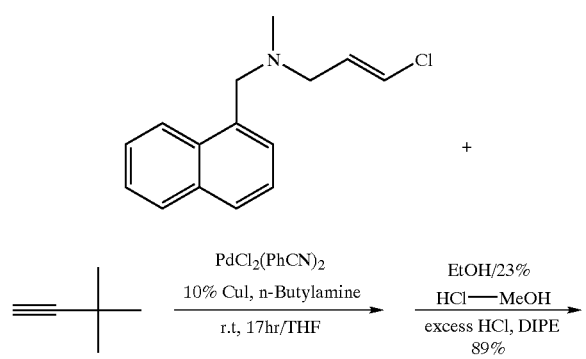

The above process employs trans-1,3-dichloropropene, which greatly increases the production cost of the final product. Further, the process is too complicated to be applied to an industrial-scale mass production.

The process disclosed in Korean Laid-open Pub. No. 2000-65,691 may be summarized as following reaction scheme 4:

Reaction Scheme 4

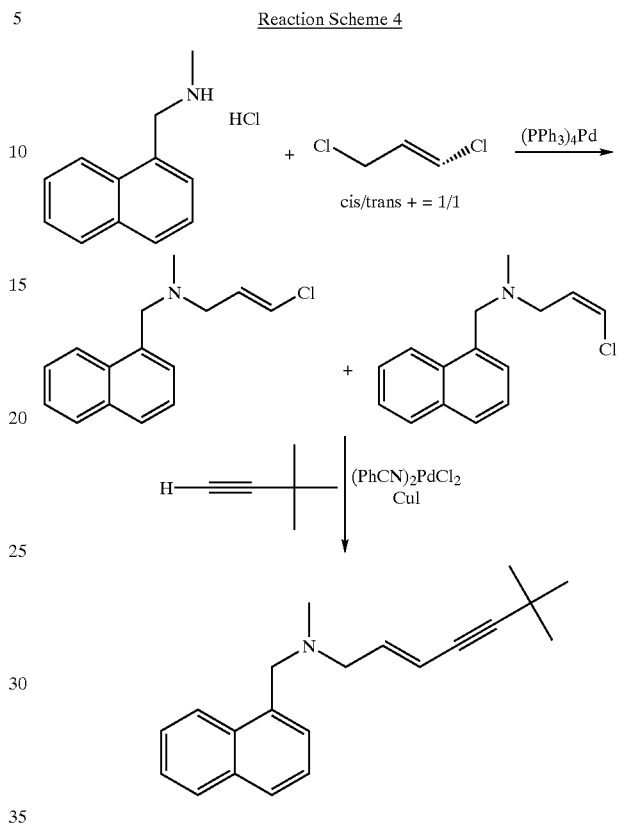

The above process employs a cis/trans mixture of 1,3-dichloropropene in order to improve the process of U.S. Pat. No. 5,440,049. However, the process may cause an environmental pollution because palladium is used in two steps as a catalyst and is also unfavorably complicated.

The process disclosed in U.S. Pat. No. 5,817,875 may be summarized as the following reaction schemes 5 and 6:

Reaction scheme 5

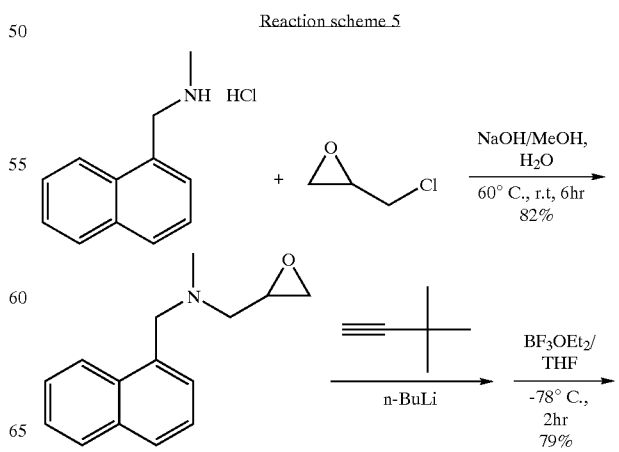

-continued

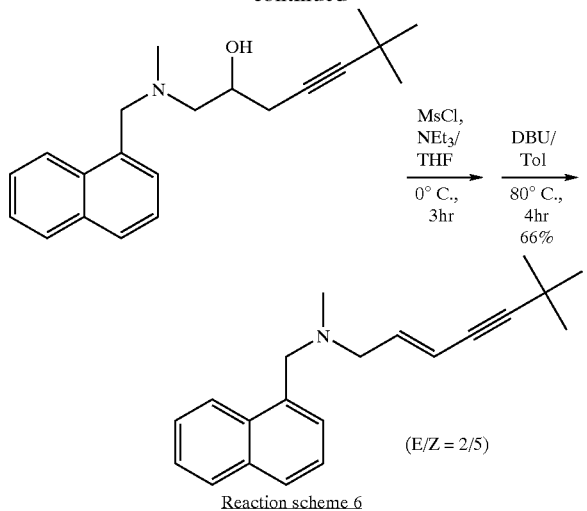

Reaction scheme 6

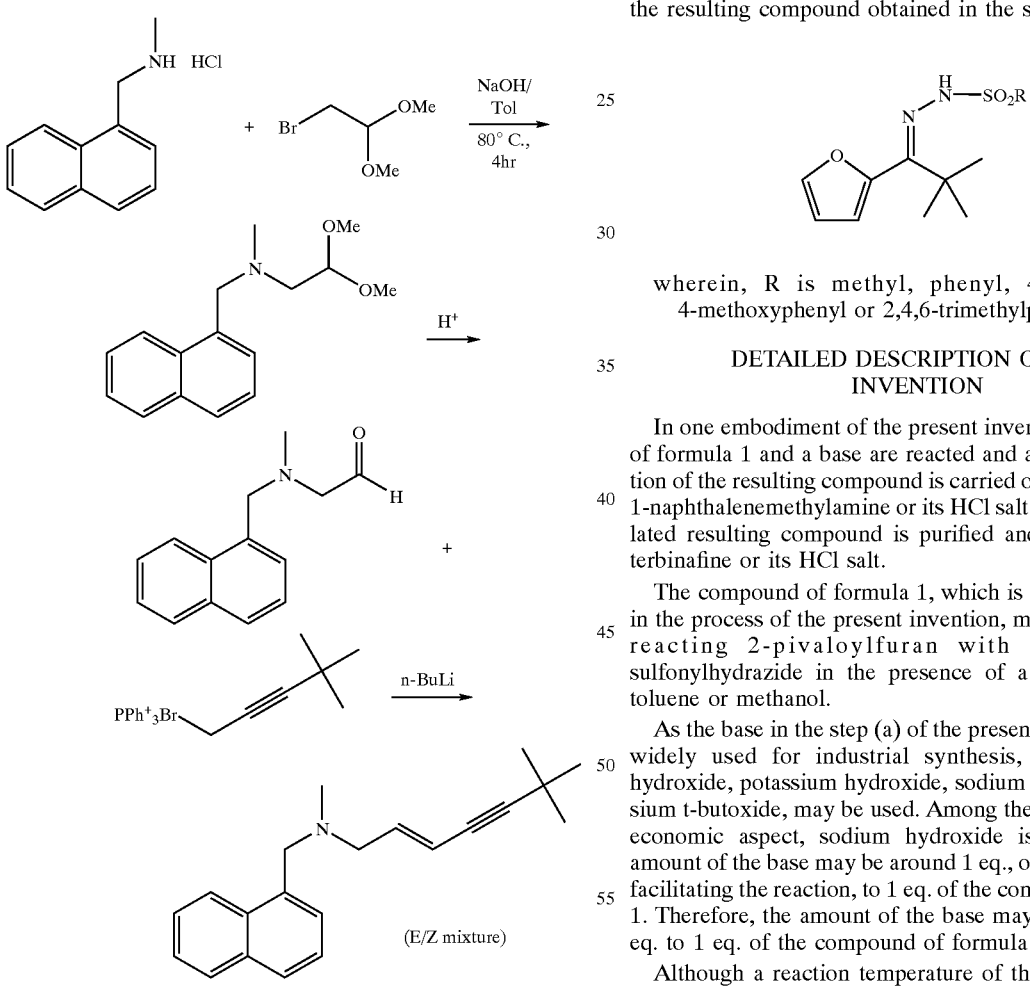

Both reactions in the above employ n-butyl-lithium difficult to be available for industrial use and the procedures are very complicated as shown in the reaction schemes 5 and 6. Further, additional isolation processes are necessary because the above processes produce a by-product.

Accordingly, the conventional processes for preparing terbinafine have many disadvantages as follows: first, strong bases such as n-butyllithium (n-BuLi) and strong reducing agent such as diisobutylaluminum hydride (DIBAL-H) are inappropriate for a mass production; second, heavy metals, such as palladium, copper or zinc, may cause an environmental pollution; third, additional reagents, such as trans-1, 3-dichloropropene, raise the cost; fourth, additional purification steps are required in order to isolate (E)-form from the (E)/(Z) mixture.

SUMMARY OF THE INVENTION

The present invention provides a process for preparing terbinafine or its HCl salt which can be performed both under a mild condition and in one pot reaction, using cheap and easily-controllable reagents, so as to be favorably applied to a large-scale mass production.

In one aspect of the present invention, there is provided a process for preparing terbinafine and/or HCl salt thereof, which comprises: (a) reacting a compound of formula 1 with a base; (b) performing a reductive alkylation of the resulting compound obtained in the step (a) with N-methyl-1-naphthalenemethylamine or its HCl salt; and (c) purifying the resulting compound obtained in the step (b):

1 wherein, R is methyl, phenyl, 4-methylphenyl, 4-methoxyphenyl or 2,4,6-trimethylphenyl.

DETAILED DESCRIPTION OF THE INVENTION

In one embodiment of the present invention, a compound of formula 1 and a base are reacted and a reductive alkylation of the resulting compound is carried out with N-methyl-1-naphthalenemethylamine or its HCl salt. Further, the alkylated resulting compound is purified and isolated to give terbinafine or its HCl salt.

The compound of formula 1, which is a starting material in the process of the present invention, may be prepared by reacting 2-pivaloylfuran with a substituted-sulfonylhydrazide in the presence of a solvent, such as toluene or methanol.

As the base in the step (a) of the present invention, a base widely used for industrial synthesis, such as sodium hydroxide, potassium hydroxide, sodium hydride, or potassium t-butoxide, may be used. Among them, considering an economic aspect, sodium hydroxide is preferable. The amount of the base may be around 1 eq., or a little excess for facilitating the reaction, to 1 eq. of the compound of formula 1. Therefore, the amount of the base may be about 0.8~2.0 eq. to 1 eq. of the compound of formula 1.

Although a reaction temperature of the step (a) may be dependent on a solvent employed, the step (a) is performed preferably at 50° C.~200° C., more preferably at 60° C.~120° C. The step (a) may be completed preferably in about 1~5 hours, more preferably about 2~3 hours.

The step (a) is performed preferably in the presence of an aprotic organic solvent, including benzene, toluene, xylene, decahydronaphthalene, acetonitrile or mixtures thereof. Among them, toluene, which is easily-controllable and cheap, is more preferable.

The reductive alkylation of the step (b) is carried out by adding N-methyl-1-naphthalenemethylamine or its HCl salt to the resulting compound obtained in the step (a). A reducing agent and an alcohol may be added thereto. Although, the eq. ratio of N-methyl-1-naphthalenemethylamine or HCl salt thereof: the compound of formula 1 may be 1:1, when considering an economic aspect, the eq. amount of N-methyl-1-naphthalenemethylamine or its HCl salt may be less than that of the compound of formula 1. Therefore, the amount of N-methyl-1-naphthalenemethylamine or its HCl salt may be about 0.25~1.0 eq. to 1 eq. of the compound of formula 1.

The reducing agent may be selected from the group consisting of sodium borohydride ($NaBH_4$), sodium triacetoxyborohydride ($NaB(OAc)_3H$), and sodium cyanoborohydride ($NaBH_3CN$). Among them, considering an economic aspect, sodium borohydride ($NaBH_4$) is more preferable. The amount of the reducing agent may be about 0.5~2.5 eq. to 1 eq. of N-methyl-1-naphthalenemethylamine or its HCl salt, more preferably 0.8~1.0 eq. to 1 eq. of N-methyl-1-naphthalenemethylamine or its HCl salt.

The alcohol includes t-butanol, isopropanol, ethanol, and methanol.

The reductive alkylation of the step (b) may be performed at room temperature or at a temperature of lower than 50° C. Further, considering purity and yield of the product, the reductive alkylation may be performed preferably at −10° C.~10° C., more preferably at −1° C.~3° C.

The purification process of the step (c) may be carried out according to conventional methods, for example, as disclosed in *J. Med. Chem.*, 1984, 27, 1539. For example, the trans form of terbinafine or its HCl salt may be isolated by organic solvent/precipitation or column chromatography. For an industrial-scale mass production, it is more preferable to purify and isolate terbinafine or its HCl salt by adding ethyl acetate to the resulting compound obtained in the step (b) and then filtering a solid precipitated thereby.

The steps (a), (b) and (c) may be carried out separately, i.e. in respective separate reactors. However, the steps (a), (b) and (c) are performed preferably in a single reactor.

Without being bound by theory, it is believed that the mechanism of the process of the present invention is as follows:

Upon reacting the compound of formula 1 with a base, the hydrazone bond is decomposed and carbenide is produced. Then, the electron pairs are rearranged and, at the same time, the oxygen-carbon bond of furan is opened, producing an aldehyde group. Neighboring double bonds are rearranged, producing a triple bond. That is, multi-step reactions voluntarily proceed to give a coupled enyne compound, which is reacted with N-methyl-1-naphthalenemethylamine or its HCl salt, in the presence of a reducing agent, to give terbinafine or its HCl salt. This process may be illustrated as the following reaction scheme 7.

Reaction scheme 7

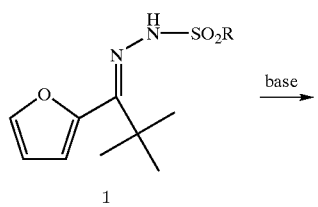

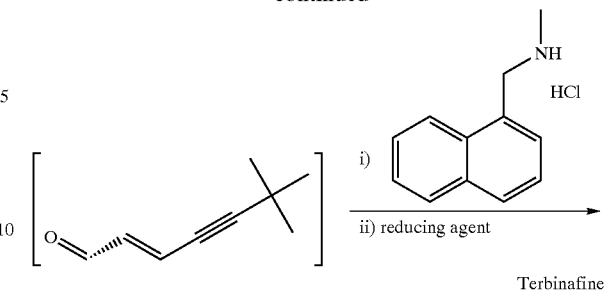

In the above reaction scheme 7, R is the same as defined in the above.

As described in the above, the process of the present invention can be carried out both under a mild condition and in one pot reaction, using cheap and easily-controllable reagents.

The present invention is further illustrated and described by the following examples, which should not be taken to limit the scope of the invention.

EXAMPLE 1

100.0 g of 2-pivaloylfuran (0.65 mol) and 73.4 g of p-toluenesulfonyl hydrazide (0.39 mol) were added to 660 ml of methanol. The reaction mixture was refluxed for six hours. After 73.4 g of p-toluensulfonyl hydrazide (0.39 mol) was added thereto, the reaction mixture was refluxed for sixteen hours. The reaction mixture was concentrated under a reduced pressure, dissolved in 600 ml of methylene chloride, washed with 600 ml of 2N-hydrochloric acid and 600 ml of distilled water, and concentrated under a reduced pressure. After the reaction mixture was crystallized with 400 ml of hexane, the resulting solid was filtered under a reduced pressure and then dried in vacuo to give 180.8 g of 1-(2'-furyl)-2,2-dimethylpropan-1-one tosyl hydrazone (yield: 85.9%).

m.p.: 82.3–83.9° C.

$^1$H NMR ($\delta$, $CDCl_3$) 7.84–7.82(m, 2H), 7.51–7.50(dd, 1H), 7.32–7.30(m, 2H), 6.67–6.66(dd, 1H), 6.51–6.50(dd, 1H), 2.43(s, 3H), 1.14(s, 9H)

EXAMPLE 2

5.0 g of 2-pivaloylfuran (32.9 mmol) and 6.79 g of benzenesulfonyl hydrazide (39.4 mmol) were added to 53 ml of methanol. The reaction mixture was refluxed for twenty-two hours. The reaction mixture was concentrated under a reduced pressure, dissolved in 30 ml of methylene chloride, washed with 30 ml of 2N-hydrochloric acid and 30 ml of distilled water, and concentrated under a reduced pressure. After the reaction mixture was crystallized with 25 ml of hexane, the resulting solid was filtered under a reduced pressure and then dried in vacuo to give 7.9 g of 1-(2'-furyl)-2,2-dimethylpropan-1-one benzenesulfonyl hydrazone (yield: 78.5%).

m.p.: 98.3–100.7° C.

$^1$H NMR ($\delta$, $CDCl_3$) 7.96–7.94(m, 2H), 7.54–7.52(m, 1H), 7.51–7.50(dd, 1H), 6.99–6.97(m, 2H), 6.67–6.66(dd, 1H), 6.51–6.50(dd, 1H), 1.13(s, 9H).

EXAMPLE 3

0.5 g of 2-pivaloylfuran (3.29 mmol) and 0.79 g of methoxybenzenesulfonyl hydrazide (3.90 mmol) were added to 30 ml of toluene. The reaction mixture was refluxed for nineteen hours. The reaction mixture was concentrated under a reduced pressure, dissolved in 10 ml of methylene chloride, washed with 10 ml of 2N-hydrochloric acid and 10 ml of distilled water, and concentrated under a reduced pressure. After the reaction mixture was crystallized with 10 ml of hexane, the resulting solid was filtered under a reduced pressure and then dried in vacuo to give 0.6 g of 1-(2'-furyl)-2,2-dimethylpropan-1-one 4-methoxybenzenesulfonyl hydrazone (yield: 56.0%).

m.p.: 145.6–146.9° C.

$^1$H NMR ($\delta$, CDCl$_3$) 7.89–7.87(m, 2H), 7.51–7.50(dd, 1H), 6.99–6.97(m, 2H), 6.67–6.66(dd, 1H), 6.51–6.50(dd, 1H), 3.87(s, 1H), 1.15(s, 9H).

EXAMPLE 4

10.02 g of 2-pivaloyl furan (65.8 mmol) and 8.7 g of methanesulfonyl hydrazide (7.90 mmol) were added to 80 ml of methanol. The reaction mixture was refluxed for nineteen hours. The reaction mixture was concentrated under a reduced pressure, dissolved in 100 ml of methylene chloride, washed with 100 ml of 2N-hydrochloric acid and 100 ml of distilled water, and was concentrated under a reduced pressure. After the reaction mixture was crystallized with 70 ml of hexane, the resulting solid was filtered under a reduced pressure and then dried in vacuo to give 9.21 g of 1-(2'-furyl)-2,2-dimethylpropan-1-one methanesulfonyl hydrazone (yield: 57.3%).

m.p.: 122.5–123.6° C.

$^1$H NMR ($\delta$, CDCl$_3$) 7.56(dd, 1H), 6.73–6.72(dd, 1H), 6.55–6.54(dd, 1H), 3.10(s, 3H), 1.26(s, 9H).

EXAMPLE 5

10.08 g of 2-pivaloylfuran (66.23 mmol) and 17.03 g of mesitylenesulfonyl hydrazide (79.47 mmol) were added to 80 ml of methanol. The reaction mixture was refluxed for nineteen hours. The reaction mixture was concentrated under a reduced pressure, dissolved in 100 ml of methylene chloride, washed with 100 ml of 2N-hydrochloric acid and 100 ml of distilled water, and concentrated under a reduced pressure. After the reaction mixture was crystallized with 70 ml of hexane, the resulting solid was filtered under a reduced pressure and then dried in vacuo to give 9.03 g of 1-(2'-furyl)-2,2-dimethylpropan-1-one 4-methoxybenzenesulfonyl hydrazone (yield: 39.1%).

m.p.: 98.4–99.5° C.

$^1$H NMR ($\delta$, CDCl$_3$) 7.54–7.53(dd, 2H), 6.95(m, 2H), 6.64–6.63(dd, 1H), 6.53–6.52(dd, 1H), 2.62(s, 6H), 2.30(s, 3H), 1.06(s, 9H).

EXAMPLE 6

The same procedures as described in Example 1 were repeated, except that hydrochloric acid (0.1 eq.) was used as a catalyst, to give 1-(2'-furyl)-2,2-dimethylpropan-1-one tosyl hydrazone (yield: 77.3%).

EXAMPLE 7

The same procedures as described in Example 1 were repeated, except that sulfuric acid (0.1 eq.) was used as a catalyst, to give 1-(2'-furyl)-2,2-dimethylpropan-1-one tosyl hydrazone (yield: 85.5%).

EXAMPLE 8

The same procedures as described in Example 1 were repeated, except that 5 g of molecular sieve was used, to give 1-(2'-furyl)-2,2-dimethylpropan-1-one tosyl hydrazone (yield: 67.0%).

EXAMPLE 9

The same procedures as described in Example 1were repeated, except that ethanol was used as a solvent, to give 1-(2'-furyl)-2,2-dimethylpropan-1-one tosyl hydrazone (yield: 46.2%).

EXAMPLE 10

The same procedures as described in Example 1 were repeated, except that toluene was used as a solvent, to give 1-(2'-furyl)-2,2-dimethylpropan-1-one tosyl hydrazone (yield: 54.3%).

EXAMPLE 11

The same procedures as described in Example 1 were repeated, except that ethyl acetate was used as a solvent, to give 1-(2'-furyl)-2,2-dimethylpropan-1-one tosyl hydrazone (yield: 85.7%).

EXAMPLE 12

The same procedures as described in Example 1 were repeated, except for reacting at 40° C., to give 1-(2'-furyl)-2,2-dimethylpropan-1-one tosyl hydrazone (yield: 55.3%).

EXAMPLE 13

The same procedures as described in Example 1 were repeated, except for reacting for twenty-eight hours, to give 1-(2'-furyl)-2,2-dimethylpropan-1-one tosyl hydrazone (yield: 82.1%).

EXAMPLE 14

5.7 g of 1-(2'-furyl)-2,2-dimethylpropan-1-one tosyl hydrazone (17.8 mmol) prepared in Example 1 and 0.8 g of sodium hydroxide (20.0 mmol) were added to 57 ml of toluene. The reaction mixture was stirred for two hours at 90° C., cooled to room temperature, and washed with 35 ml of distilled water and 35 ml of 2N-hydrochloride acid (twice). 2.8 g of N-methyl-1-naphthalenemethylamine hydrochloride (13.5 mmol) and 0.43 g of sodium borohydride (NaBH$_4$, 11.3 mmol) were added to the reaction mixture, which was then stirred for an hour at room temperature. 15 ml of methanol was added to the reaction mixture, which was then stirred for fifteen hours at room temperature, washed with 50 ml of 2N-hydrochloric acid twice, and concentrated under a reduced pressure. 25 ml of ethyl acetate was added to the reaction mixture, which was then stirred for an hour to produce a solid. The resulting solid was filtered under a reduced pressure, washed with 25 ml of ethyl acetate, and then dried in vacuo to give 0.46 g of terbinafine hydrochloride (yield: 10.4%)

$^1$H NMR ($\delta$, CDCl$_3$) 12.78(s, 1H), 8.13–8.06(m, 2H), 7.97–7.92(m, 2H), 7.65–7.63(m, 1H), 7.59–7.57(m, 2H), 6.39–6.35(m, 1H), 5.89–5.85(d, 1H), 4.78–4.75(m, 1H), 4.62–4.63(m, 1H), 3.88–3.87(m, 1H), 3.66–3.65(m, 1H), 2.63(s, 3H), 1.24(s, 9H).

EXAMPLE 15

7 g of 1-(2'-furyl)-2,2-dimethylpropan-1-one benzenesulfonyl hydrazone (22.9 mmol) prepared in Example 2 and 1.0 g of sodium hydroxide (25.0 mmol) were added to 35 ml of toluene. The reaction mixture was stirred for two hours at 90° C., cooled to room temperature and washed with 35 ml of distilled water and 35 ml of 2N-hydrochloride acid (twice). 3.5 g of N-methyl-1-naphthalenemethylamine hydrochloride (16.9 mmol) and 0.54 g of sodium borohydride (14.3 mmol) were added to the reaction mixture, which was then stirred for an hour at room temperature. 19 ml of isopropanol were added to the reaction mixture, which was then stirred for thirty-five hours at room temperature, washed with 35 ml of 2N-hydrochloric acid twice, and concentrated under a reduced pressure. 35 ml of ethyl acetate were added to the reaction mixture, which was then stirred for an hour to produce a solid. The resulting solid was filtered under a reduced pressure, washed with 35 ml of ethyl acetate, and then dried in vacuo to give 1.03 g of terbinafine hydrochloride (yield: 18.6%).

EXAMPLE 16

0.5 g of 1-(2'-furyl)-2,2-dimethylpropan-1-one 4-methoxybenzenesulfonyl hydrazone (1.49 mmol) prepared in Example 3 and 0.06 g of sodium hydroxide (1.59 mmol) were added to 10 ml of toluene. The reaction mixture was stirred for two hours at 90° C., cooled to room temperature, and washed with 10 ml of distilled water and 10 ml of 2N-hydrochloride acid (twice). 0.23 g of N-methyl-1-naphthalenemethylamine hydrochloride (1.11 mmol) and 0.04 g of sodium borohydride (1.1 mmol) were added to the reaction mixture, which was then stirred for an hour at room temperature. 14 ml of isopropanol was added to the reaction mixture, which was then stirred for thirty-six hours at room temperature, washed with 35 ml of 2N-hydrochloric acid twice, and concentrated under a reduced pressure. The resulting mixture was purified with silica gel column chromatography (ethyl acetate/hexane=1/20) to give 0.03 g of terbinafine (yield: 9.3%).

EXAMPLE 17

7.7 g of 1-(2'-furyl)-2,2-dimethylpropan-1-one methanesulfonyl hydrazone (31.5 mmol) prepared in Example 4 and 1.4 g of sodium hydroxide (34.7 mmol) were added to 40 ml of toluene. The reaction mixture was stirred for two hours at 90° C., cooled to room temperature, and washed with 40 ml of distilled water and 40 ml of 2N-hydrochloride acid (twice). 5.2 g of N-methyl-1-naphthalenemethylamine hydrochloride (25.2 mmol) and 0.95 g of sodium borohydride (25.2 mmol) were added to the reaction mixture, which was then stirred for an hour at room temperature. 20 ml of isopropanol was added to the reaction mixture, which was then stirred for thirty-six hours at room temperature, washed with 40 ml of 2N-hydrochloric acid twice, concentrated under a reduced pressure. 40 ml of ethyl acetate were added to the reaction mixture, which was then stirred for an hour to produce a solid. The resulting solid was filtered under a reduced pressure, washed with 40 ml of ethyl acetate, and then dried in vacuo to give 0.9 g of terbinafine hydrochloride (yield: 10.9%).

EXAMPLE 18

8.0 g of 1-(2'-furyl)-2,2-dimethylpropan-1-one 4-methoxybenzenesulfonyl hydrazone (23.0 mmol) prepared in Example 5 and 1.0 g of sodium hydroxide (25.3 mmol) were added to 40 ml of toluene. The reaction mixture was stirred for two hours at 90° C., cooled to room temperature, and washed with 40 ml of distilled water and 40 ml of 2N-hydrochloride acid twice. 3.5 g of N-methyl-1-naphthalenemethylamine hydrochloride (18.3 mmol) and 0.54 g of sodium borohydride (14.2 mmol) were added to the reaction mixture, which was then stirred for an hour at room temperature. 19 ml of isopropanol was added to the reaction mixture, which was then stirred for thirty-six hours at room temperature, washed with 40 ml of 2N-hydrochloric acid twice, and concentrated under a reduced pressure. 40 ml of ethyl acetate was added to the reaction mixture, which was then stirred for an hour to produce a solid. The resulting solid was filtered under a reduced pressure, washed with 35 ml of ethyl acetate, and then dried in vacuo to give 0.7 g of terbinafine hydrochloride (yield: 11.7%).

EXAMPLE 19

The same procedures as described in Example 14 were repeated, except that ethanol was used instead of methanol, to give 0.75 g of terbinafine hydrochloride (yield: 16.9%).

EXAMPLE 20

The same procedures as described in Example 14 were repeated, except that isopropanol was added to the reaction mixture instead of methanol and then reacted for thirty-nine hours, to give 1.02 g of terbinafine hydrochloride (yield: 23.0%).

EXAMPLE 21

The same procedures as described in Example 14 were repeated, except that t-butanol was used instead of methanol and then reacted for sixty-three hours, to give 1.58 g of terbinafine hydrochloride (yield: 35.7%).

EXAMPLE 22

The same procedures as described in Example 14 were repeated, except that sodium triacetoxyborohydride was used instead of sodium borohydride, to give 1.32 g of terbinafine hydrochloride (yield: 30.0%).

EXAMPLE 23

The same procedures as described in Example 14 were repeated, except that sodium cyanoborohydride was used instead of sodium borohydride, to give 1.2 g of terbinafine hydrochloride (yield: 27.1%).

EXAMPLE 24

The same procedures as described in Example 14 were repeated, except that N-methyl-1-naphthalenemethylamine was used instead of N-methyl-1-naphthalenemethylamine hydrochloride, to give 0.39 g of terbinafine hydrochloride (yield: 8.8%).

EXAMPLE 25

The same procedures as described in Example 14 were repeated, except that sodium hydride was used instead of sodium hydroxide, to give 0.48 g of terbinafine hydrochloride (yield: 10.8%).

EXAMPLE 26

The same procedures as described in Example 14 were repeated, except that acetonitrile was used instead of toluene, to give 0.42 g of terbinafine hydrochloride (yield: 9.5%).

EXAMPLE 27

5.7 g of 1-(2'-furyl)-2,2-dimethylpropan-1-one tosyl hydrazone (17.8 mmol) prepared in Example 1 and 0.89 of sodium hydroxide (20.0 mmol) were added to 57 ml of toluene. The reaction mixture was stirred for two hours at 90° C., cooled to room temperature, and washed with 30 ml of distilled water and 30 ml of 2N-hydrochloric acid. 2.8 g of N-methyl-1-naphthalenemethylamine hydrochloride (13.5 mmol), 0.8 ml of acetic acid and 0.43 g of sodium borohydride (11.3 mmol) were added to the reaction mixture, which was then stirred for an hour at room temperature. 15 ml of t-butanol was added to the reaction mixture, which was then stirred for twenty-four hours at room temperature, washed with 50 ml of 2N-hydrochloric acid twice, and concentrated under a reduced pressure. 25 ml of ethyl acetate was added to the reaction mixture, which was then stirred for an hour to produce a solid. The resulting solid was filtered under a reduced pressure, washed with 25 ml of ethyl acetate, and then dried in vacuo to give 0.77 g of terbinafine hydrochloride (yield: 17.4%).

EXAMPLE 28

5.7 g of 1-(2'-furyl)-2,2-dimethylpropan-1-one tosyl hydrazone (17.8 mmol) prepared in Example 1 and 0.8 g of sodium hydroxide (20.0 mmol) were added to 57 ml of toluene. The reaction mixture was stirred for two hours at 90° C., cooled to room temperature, and washed with 30 ml of distilled water and 30 ml of 2N-hydrochloric acid. 2.8 g of N-methyl-1-naphthalenemethylamine hydrochloride (13.5 mmol) and 0.43 g of sodium borohydride (11.3 mmol). were added to the reaction mixture, which was then stirred for an hour at room temperature. 15 ml of t-butanol was added to the reaction mixture, which was then stirred for twenty-four hours at 60° C., washed with 50 ml of 2N-hydrochloric acid twice, and concentrated under a reduced pressure. 25 ml of ethyl acetate was added to the reaction mixture, which was then stirred for an hour to produce a solid. The resulting solid was filtered under a reduced pressure, washed with 25 ml of ethyl acetate, and then dried in vacuo to give 0.84 g of terbinafine hydrochloride (yield: 19.0%).

EXAMPLE 29

11.4 g of 1-(2'-furyl)-2,2-dimethylpropan-1-one tosyl hydrazone (35.6 mmol) prepared in Example 1 and 1.6 g of sodium hydroxide (40.0 mmol) were added to 57 ml of toluene. The reaction mixture was stirred for two hours at 90° C., cooled to room temperature, and washed with 60 ml of distilled water. 2.8 g of N-methyl-1-naphthalenemethylamine hydrochloride (13.5 mmol) and 0.98 g of sodium borohydride (25.9 mmol) were added to the reaction mixture, which was then stirred for an hour at room temperature. 30 ml of ethanol was added to the reaction mixture, which was then stirred for twenty-four hours at room temperature, washed with 50 ml of 2N-hydrochloric acid twice, and concentrated under a reduced pressure. 40 ml of ethyl acetate were added to the reaction mixture, which was then stirred for an hour to produce a solid. The resulting solid was filtered under a reduced pressure, washed with 40 ml of ethyl acetate, and then dried in vacuo to give 2.0 g of terbinafine hydrochloride (yield: 45.5%).

EXAMPLE 30

17.1 g of 1-(2'-furyl)-2,2-dimethylpropan-1-one tosyl hydrazone (53.4 mmol) prepared in Example 1 and 2.4 g of sodium hydroxide (60.0 mmol) were added to 57 ml of toluene. The reaction mixture was stirred for two hours at 90° C., cooled to room temperature, and washed with 90 ml of distilled water. 2.8 g of N-methyl-1-naphthalenemethylamine hydrochloride (13.5 mmol) and 0.98 g of sodium borohydride (25.9 mmol) were added to the reaction mixture, which was then stirred for an hour at room temperature. 15 ml of isopropanol was added to the reaction mixture, which was then stirred for twenty-four hours at room temperature, washed with 50 ml of 2N-hydrochloric acid twice, and concentrated under a reduced pressure. 40 ml of ethyl acetate was added to the reaction mixture, which was then stirred for an hour to produce a solid. The resulting solid was filtered under a reduced pressure, washed with 40 ml of ethyl acetate, and then dried in vacuo to give 2.2 g of terbinafine hydrochloride (yield: 50.3%).

EXAMPLE 31

The same procedures as described in Example 14 were repeated, except that potassium hydroxide was used instead of sodium hydroxide, to give 0.47 g of terbinafine hydrochloride (yield: 10.6%).

EXAMPLE 32

The same procedures as described in Example 14 were repeated, except that potassium t-butoxide was used instead of sodium hydroxide, to give 0.44 g of terbinafine hydrochloride (yield: 9.9%).

EXAMPLE 33

The same procedures as described in Example 14 were repeated, except that benzene was used instead of toluene, to give 0.48 g of terbinafine hydrochloride (yield: 10.8%).

EXAMPLE 34

The same procedures as described in Example 14 were repeated, except that xylene was used instead of toluene, to give 0.44 g of terbinafine hydrochloride (yield: 9.9%).

EXAMPLE 35

The same procedures as described in Example 14 were repeated, except that decahydronaphthalene was used instead of toluene, to give 0.42 g of terbinafine hydrochloride (yield: 9.5%).

EXAMPLE 36

The same procedures as described in Example 30 were repeated, except that the reaction mixture was stirred for thirty-two hours at about −5° C. instead of being stirred for twenty-four hours at room temperature, to give 2.4 g of terbinafine hydrochloride (yield: 54.2%).

EXAMPLE 37

The same procedures as described in Example 30 were repeated, except that the reaction mixture was stirred for twenty-eight hours at about 3° C. instead of being stirred for twenty-four hours at room temperature, to give 2.4 g of terbinafine hydrochloride (yield: 53.0%).

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A method for preparing terbinafine or its HCl salt comprising:

(a) reacting a compound of formula 1 with a base

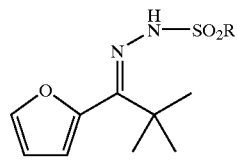

1 wherein R is methyl, phenyl, 4-methylphenyl, 4-methoxyphenyl or 2,4,6-trimethylphenyl; and (b) performing a reductive alkylation of the resulting compound obtained in the step (a) with N-methyl-1-naphthalenemethylamine or its HCl salt.

2. The method of claim 1, wherein the preparation is performed in a single reactor.

3. The method of claim 1, wherein the base is selected from the group consisting of sodium hydroxide, potassium hydroxide, sodium hydride and potassium t-butoxide.

4. The method of claim 1, wherein reacting the compound of formula 1 with the base is carried out at 50° C. to 200° C.

5. The method of claim 1, wherein reacting the compound of formula 1 with the base is performed in the presence of an aprotic organic solvent.

6. The method of claim 5, wherein the aprotic organic solvent is selected from the group consisting of benzene, toluene, xylene, decahydronaphthalene and acetonitrile.

7. The method of claim 1, wherein an amount of N-methyl-1-naphthalenemethylamine or its HCl salt is 0.25~1.0 eq. to 1 eq. of the compound of formula 1.

8. The method of claim 1, wherein performing the reductive alkylation is carried out at −10° C. to 10° C.

9. The method of claim 1, wherein performing the reductive alkylation is performed in the presence of a reducing agent selected from the group consisting of sodium borohydride, sodium triacetoxyborohydride and sodium cyanoborohydride and an alcohol.

10. The method of claim 9, wherein the reducing agent is sodium borohydride.

11. The method of claim 9, wherein an amount of the reducing agent is 0.5~2.5 eq. to 1 eq. of N-methyl-1-napthalenemethylamine or its HCl salt.

12. The method of claim 9, wherein the alcohol is selected from the group consisting or t-butanol, isopropanol, ethanol and methanol.

13. The method of claim 1, further comprising:

(c) adding ethyl acetate to the resulting compound in the step (b) to form a solid; and (d) filtering the solid.

* * * * *